(12) United States Patent
Dossa

(10) Patent No.: US 6,338,724 B1
(45) Date of Patent: Jan. 15, 2002

(54) ARTERIO-VENOUS INTERCONNECTION

(76) Inventor: Christos D. Dossa, 333 E. 69th St., Apt. 4F, New York, NY (US) 10021

( * ) Notice: Subject to any disclaimer, the term of this patent is extended or adjusted under 35 U.S.C. 154(b) by 0 days.

(21) Appl. No.: 09/280,398

(22) Filed: Mar. 29, 1999

(51) Int. Cl.⁷ .......................... A61M 5/00; A61M 37/00; A61F 2/06
(52) U.S. Cl. .......................... 604/8; 604/6.16; 623/1.16; 623/1.3
(58) Field of Search ...................... 623/1, 1.1, 1.3–1.31; 604/8–10, 523, 4.01, 6.16; 128/898

(56) References Cited

U.S. PATENT DOCUMENTS

| | | | |
|---|---|---|---|
| 3,409,913 A | 11/1968 | Kantrowitz et al. | |
| 3,638,649 A | 2/1972 | Ersek | |
| 3,713,441 A | 1/1973 | Thomas | |
| 3,818,511 A | * | 6/1974 | Goldberg et al. |
| 3,826,257 A | 7/1974 | Buselmeier | |
| 3,853,126 A | 12/1974 | Schulte | |
| 3,882,862 A | 5/1975 | Berend | |
| 4,490,137 A | * | 12/1984 | Moukheibir |
| 4,501,263 A | 2/1985 | Harbuck | |
| 4,619,641 A | 10/1986 | Schanzer | |
| 4,643,712 A | 2/1987 | Kulik et al. | |
| 4,772,269 A | 9/1988 | Twardowski et al. | |
| 4,808,163 A | 2/1989 | Laub | |
| 4,816,339 A | 3/1989 | Tu et al. | |
| 4,882,113 A | 11/1989 | Tu et al. | |
| 5,024,671 A | 6/1991 | Tu et al. | |
| 5,041,098 A | 8/1991 | Loiterman et al. | |
| 5,057,073 A | 10/1991 | Martin | |
| 5,152,782 A | 10/1992 | Kowligi et al. | |
| 5,192,310 A | 3/1993 | Herweck et al. | |
| 5,209,723 A | 5/1993 | Twardowski et al. | |
| 5,360,397 A | 11/1994 | Pinchuk | |
| 5,370,681 A | 12/1994 | Herweck et al. | |
| 5,376,110 A | 12/1994 | Tu et al. | |
| 5,591,226 A | 1/1997 | Trerotola et al. | |
| 5,620,763 A | 4/1997 | House et al. | |
| 5,628,782 A | 5/1997 | Myers et al. | |
| 5,628,786 A | 5/1997 | Banas et al. | |
| 5,641,373 A | 6/1997 | Shannon et al. | |
| 5,713,859 A | 2/1998 | Finch, Jr. et al. | |
| 5,755,780 A | 5/1998 | Finch, Jr. et al. | |
| 5,782,811 A | * | 7/1998 | Samson et al. ............. 604/282 |
| 5,800,409 A | 9/1998 | Bruce | |
| 5,800,522 A | * | 9/1998 | Campbell et al. ............... 623/1 |
| 6,019,788 A | * | 2/2000 | Butters et al. |

FOREIGN PATENT DOCUMENTS

WO    WO 98/34676    8/1998

OTHER PUBLICATIONS

A.S. Coulson, M.D., et al., "A Combination of the Elephant Trunk Anastomosis Technique and Vascular Clips for Dialysis Grafts", Surgical Rounds, Nov. 1999; pp. 596–608.

* cited by examiner

Primary Examiner—Angela D. Sykes
Assistant Examiner—Patricia Bianco
(74) Attorney, Agent, or Firm—Fish & Richardson P.C.

(57) ABSTRACT

Apparatus and methods for interconnecting an artery and a vein by means of a graft of biocompatible material and a catheter of biocompatible material. The graft has an end configured for attachment to the artery and another end configured for interconnection with the catheter. The catheter has an end configured for interconnection with the graft and has at least one hole spaced axially therefrom that is positionable within the interior of the vein and spaced from an opening of the vein through which the catheter passes into the vein. The at least one hole provides an outlet within the interior of the vein for blood from the artery that passes through the graft and the catheter. The catheter and graft may be provided as a combined assembly, or the catheter may be inserted through the wall of an existing graft in order to salvage the existing graft.

37 Claims, 7 Drawing Sheets

ARTERIO-VENOUS INTERCONNECTION

BACKGROUND OF THE INVENTION

This invention relates to an apparatus and method for interconnecting an artery and vein, and more particularly to providing, through such an interconnection, an artificial access to a patient's bloodstream for hemodialysis.

The United States Renal Data System has estimated the number of patients with end-stage renal disease (ESRD) in 1989, including those with functioning kidney transplants, to be greater than 200,000. Since the inception of hemodialysis for end-stage renal disease, various types of arterio-venous (AV) conduits have been provided to provide access to the bloodstream. Various access options have been used, including external arterio-venous shunts, native arterio-venous fistulas, and various arterio-venous grafts (AVG) such as reverse saphenous vein, bovine heterograft, DACRON, and expanded polytetraflouroethylene (ePTFE). The grafts function as artificial vessels into which needles can be repeatedly inserted (such as about three times per week) to allow blood to be removed from a patient's bloodstream, and to allow the blood to be returned to the patient's bloodstream after it has passed through a hemodialysis machine. These grafts typically have one end connected to an incision on the wall of an artery and another end connected to an incision on the wall of a vein.

In certain hemodialysis patients, autogenous fistulas cannot be constructed. PTFE is a graft material of choice for such patients.

Thus, arterio-venous grafts, as opposed to creation of fistulas, are used in a substantial portion of the end-stage renal disease population, although this portion of the population varies from country to country.

Many arterio-venous grafts (AVGs) have patency rates of about two years. Thrombotic complications associated with such grafts contribute to hospital admissions for end-stage renal disease patients.

The patency of arterio-venous grafts can be maintained or re-established by interventions including lytic therapy, angioplasty, stenting, mechanical thrombectomy, and operative revision. Of course, there are costs associated with these interventions.

Outflow obstruction caused by intimal hyperplasia at the graft-venous connection (anastomosis) can cause arterio-venous grafts to fail. The above-listed interventions can be used as sub-optimal remedies for intimal hyperplasia, at some cost.

SUMMARY OF THE INVENTION

The invention provides apparatus and methods for interconnecting an artery and a vein. The apparatus includes a graft of biocompatible material and a catheter of biocompatible material. The graft has an end configured for attachment to the artery and another end configured for interconnection with the catheter. The catheter has an end configured for interconnection with the graft and has at least one hole spaced axially therefrom that is positionable within the interior of the vein and spaced from an opening of the vein through which the catheter passes into the vein. The at least one hole provides an outlet within the interior of the vein for blood from the artery that passes through the graft and the catheter.

The invention has the potential to decrease substantially the arterio-venous graft (AVG) failure rate due to venous outflow tract stenosis in end-stage renal disease (ESRD) hemodialysis patients. In particular, the invention can potentially reduce arterio-venous graft failure resulting from venous outflow tract stenosis. This result is accomplished by avoiding a graft-to-vein sutured connection (anastomosis) and instead employing a catheter introduced into the interior of the vein through a small puncture hole on the wall of the vein.

It is believed that venous outflow obstruction secondary to myointimal hyperplasia may be caused by 1) high-flow turbulent blood passing through the graft-to-vein sutured connection (anastomosis) 2) trauma to the vein wall incurred by the suturing and surgical handling of the vein and 3) compliance mismatch between a relatively thick and rigid ePTFE graft and a thin elastic vein.

The present invention avoids the above-listed factors by 1) distributing the high blood flow over a longer segment of vein through side holes on the catheter; 2) limiting vein wall trauma to a single puncture hole and 3) ensuring that the catheter sits on the interior of the vein, thereby avoiding compliance mismatch problems.

Due to the reduction of venous outflow obstruction, it is anticipated that the invention can improve patency rates and lead to substantial reduction in hospital admissions and the cost of interventions such as lytic therapy, angioplasty, stenting, mechanical thrombectomies, and operative revisions. As a result, it is expected that the invention can markedly reduce morbidity, mortality, and cost among end-stage renal disease patents.

The catheter and graft of the present invention may be provided as a combined assembly, or, in a modification of the invention, the catheter may be inserted through the wall of an existing graft in order to salvage the existing graft. When an existing arterio-venous graft (AVG) is failing due to venous outflow obstruction, the modified invention can salvage the graft. In particular, one specific implementation of the invention for salvaging of the graft is as follows: the graft is percutaneously cannulated by conventional means and the graft-to-venous connection (anastomosis) is angio-plastied. Via the existing sheath and guide wire used for the angioplasty a catheter that is funnel-shaped on one end and has side holes on the other end is inserted through the graft-to-vein connection (anastomosis). The funnel-shaped part of the catheter lies in the pre-existing graft and the slim end (tail) lies in the interior of the vein. The resulting modified assembly accomplishes complete bypass (exclusion) of the graft-to-vein connection (anastomosis), and any subsequent myointimal restenosis should not affect venous outflow.

Numerous other features, objects, and advantages of the invention will become apparent from the following detailed description when read in connection with the accompanying drawings.

DETAILED DESCRIPTION

Figure 1:
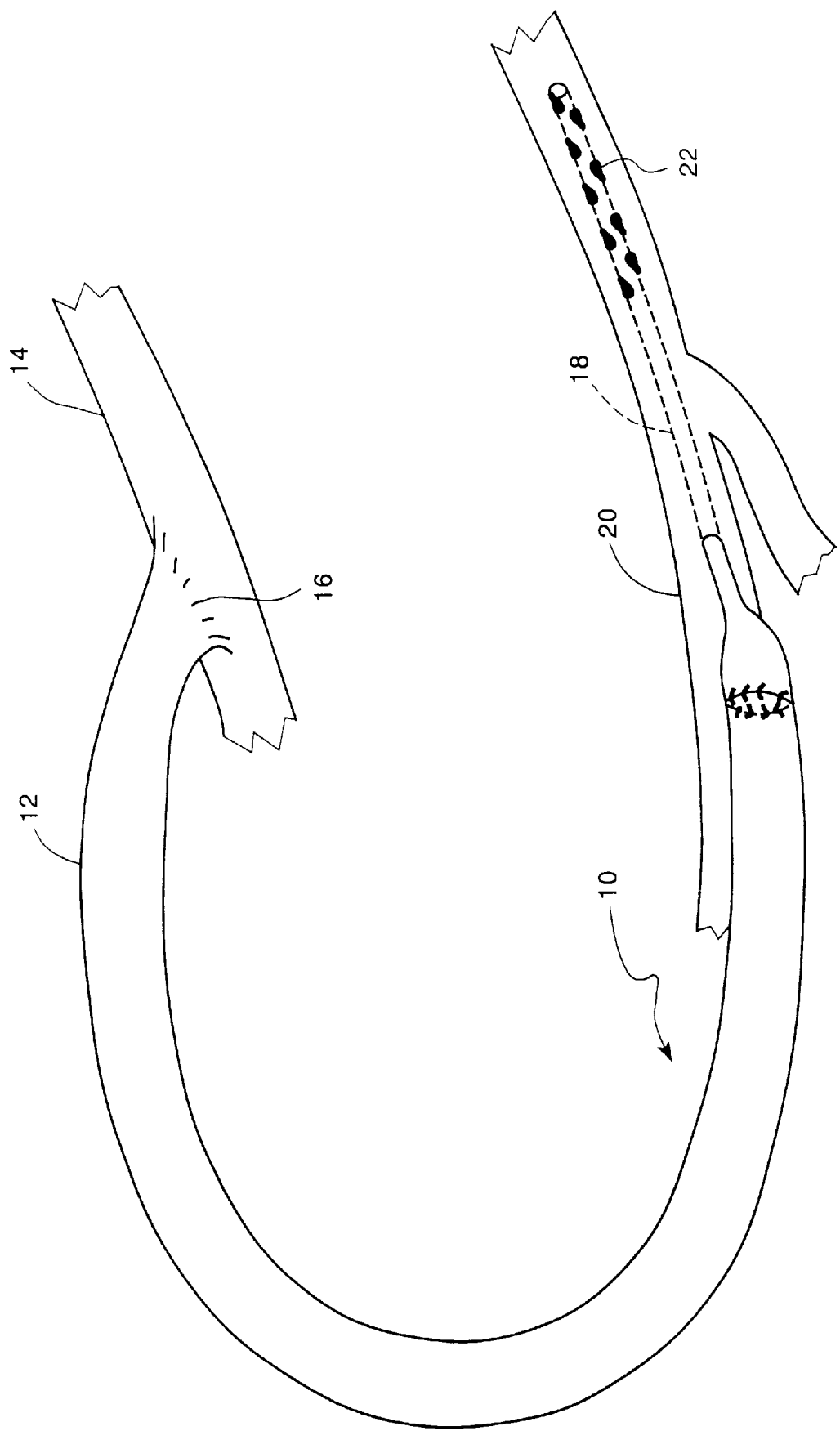
FIG. 1 is a drawing of an apparatus according to the invention interconnecting an artery and a vein.

With reference to FIG. 1, an apparatus 10 according to the invention includes an artificial subcutaneous graft 12 that has one end attached to an artery 14. The other end of artificial graft 12 is attached to an end of an elastic intravascular catheter 18. There may be a mechanical attachment of graft 12 to catheter 18, such as a snap-on connection, or graft 12 and catheter 18 may be manufactured as an integral unit. Alternatively, the graft-to-catheter connection may be hand-sewn. Intravascular catheter 18 passes through an incision in a side wall of vein 20 and extends within the vein. Intravascular catheter 18 has a number of small holes 22 in its side wall through which blood from artery 14 enters vein 20.

Graft 12 may be constructed of a relatively thin wall of polytetraflouroethylene (PTFE) and may be sutured to artery 14. The entrance of vein 20 may be attached to catheter 18 by a small number of sutures, or in certain circumstances no sutures may be required. Graft 12 may typically have a length of about 20 to 40 centimeters or longer and an outer diameter of about 6 millimeters. Intravascular catheter 18 may likewise be constructed of a relatively thin wall of PTFE or SILASTIC or standard catheter materials. Catheter 18 may enter a peripheral vein and the tip of catheter 18 may extend into a larger central vein. Catheter 18, which may flare outward at its connection with graft 12, may have a length of about 10 to 40 centimeters and a diameter of about 6 to 14 French at its thinner end, depending on the anatomy of the particular patient in which apparatus 10 is to be implanted (see discussion below). Catheter 18 may have a funnel configuration; for example, the outer diameter of the end that is connected to graft 12 may be about 16 french and the diameter of the other end may be about 12 french. Graft 12 may be connected to catheter 18 mechanically or may be integral with catheter 18. Subcutaneous graft 12, like known arterio-venous grafts, functions as an artificial vessel into which needles can be repeatedly inserted as described above.

Because apparatus 10 does not force high-pressure blood into the entrance of vein. 20, but instead allows the blood to exit through holes 22 in catheter 18 at locations downstream from the entrance to vein 20, apparatus 10 provides reduced scarring and stenosis at the entrance of vein 20. In particular, apparatus 10 minimizes flow turbulence within vein 20, especially in the sensitive area at which the vein is connected to plastic catheter 18. The connection between catheter 18 and the wall of vein 20 will not have to experience a high flow turbulence.

Figure 2:
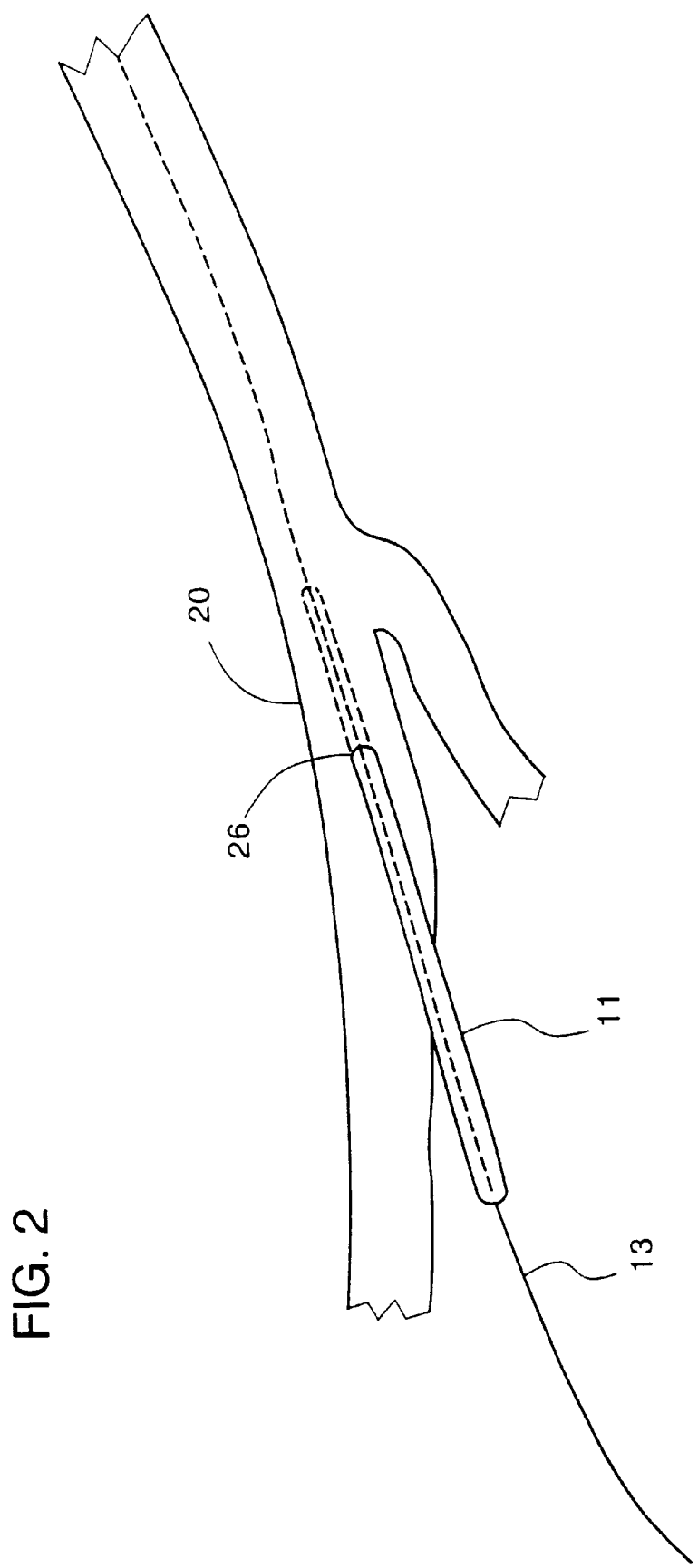
FIG. 2 is a drawing of an artery and a vein in which a guidewire has been inserted through an incision into the vein in order to permit interconnection of the vein with the apparatus shown in FIG. 1.
Figure 3:
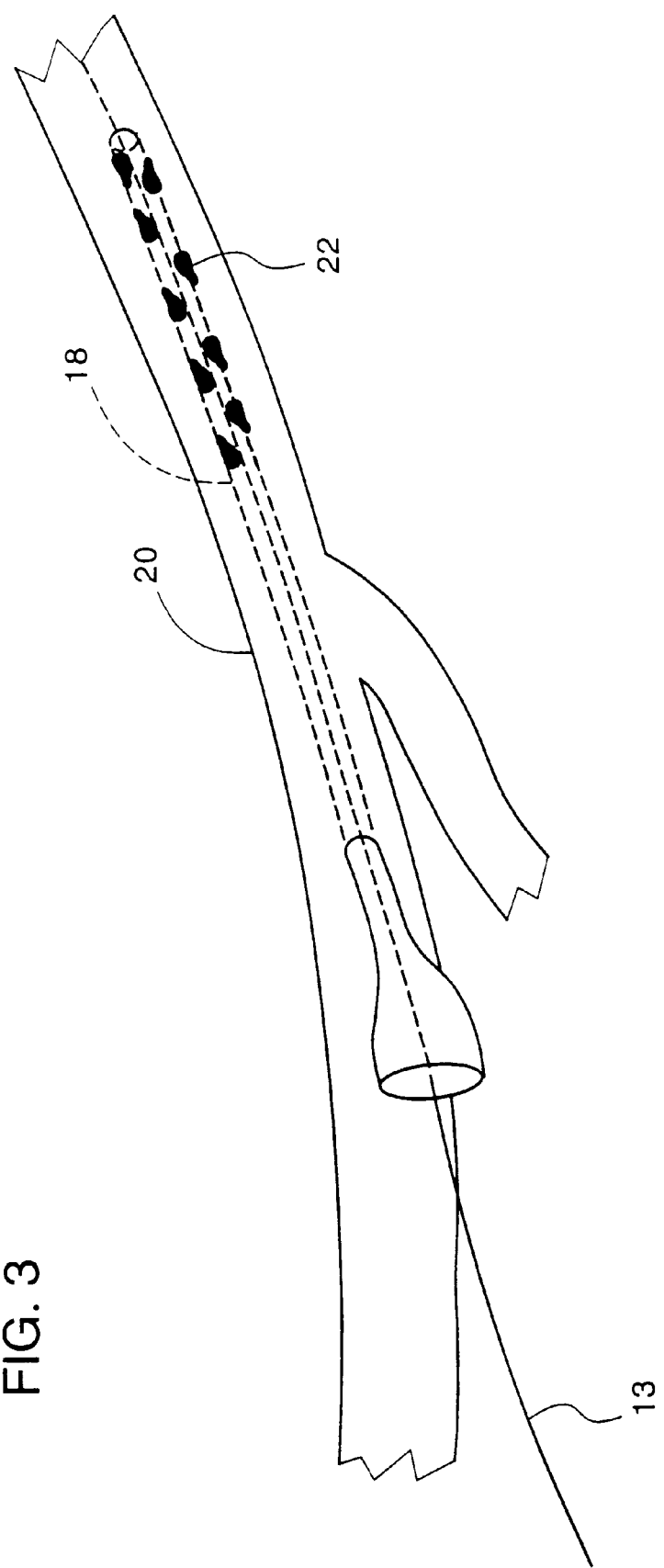
FIG. 3 is a drawing of the artery and vein of FIG. 2, further showing the apparatus according to the invention shown in FIG. 1 inserted into the vein.

As shown in FIG. 2, in the procedure for attaching apparatus 10 to artery 14 and vein 20, a needle 11 is passed through an incision 26 into vein 20, and a guidewire 13 is passed through needle 11 into vein 20. Incision 26 is dilated, and, as shown in FIG. 3, catheter 18 is threaded through vein 20. Next, an incision is made in artery 14, and the end of graft 12 is securely attached to the incision in artery 14 by a set of sutures 16 to produce the configuration of FIG. 1. Because of differences in vein anatomy in different patients, it may be desirable to select one of a set of apparatuses 10 having catheters 18 of differing lengths, in order to ensure that holes 22 are properly positioned. In patients with severe vein scar tissue, catheter 18 can be threaded through the scar tissue. Thus, apparatus 10 is especially useful for such patients with severe scarring of vein 20.

Figure 4:
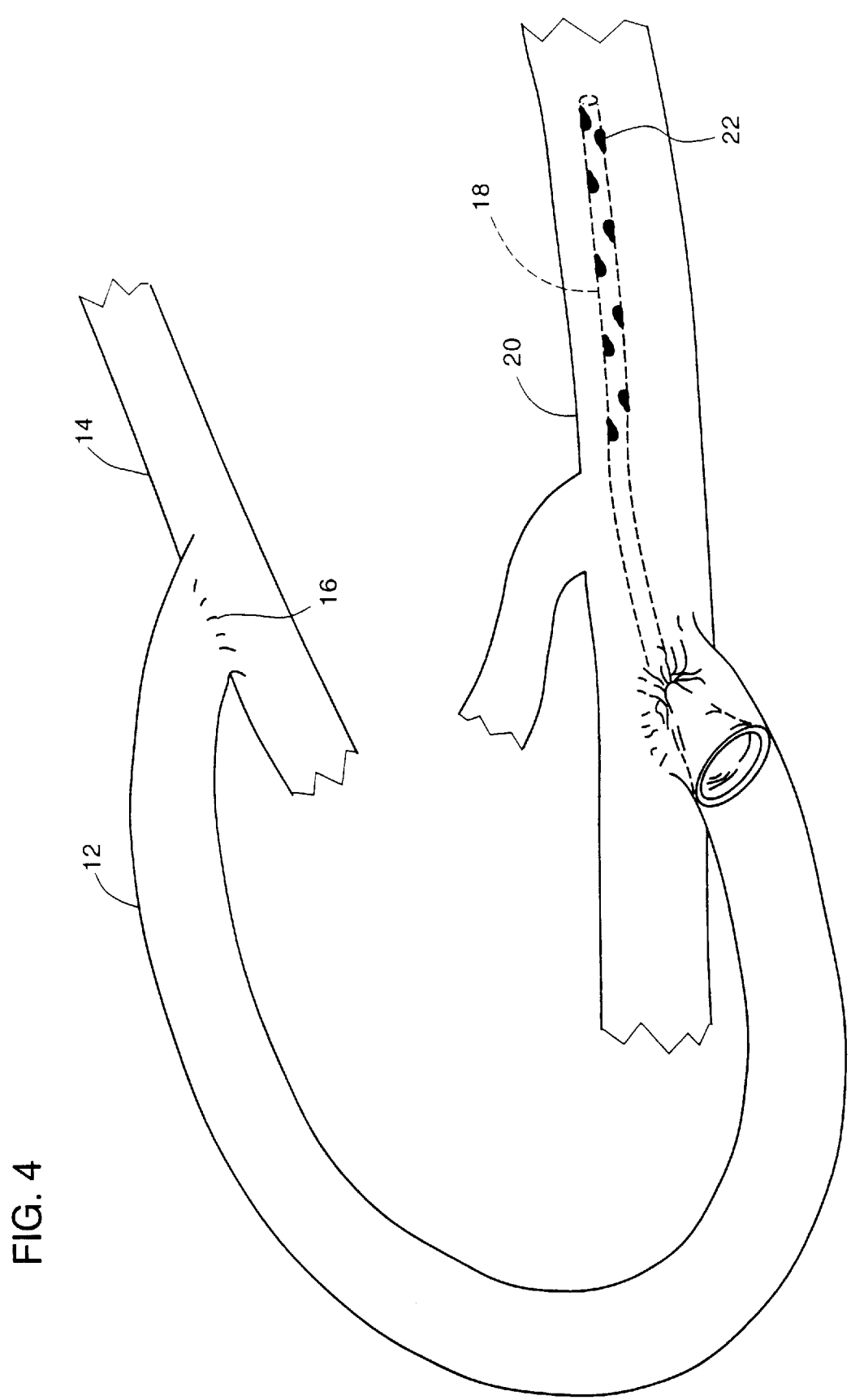
FIG. 4 is a drawing of an artery, a vein, a preexisting graft, and a catheter according to the invention provided for the purpose of salvaging the existing graft.
Figure 5:
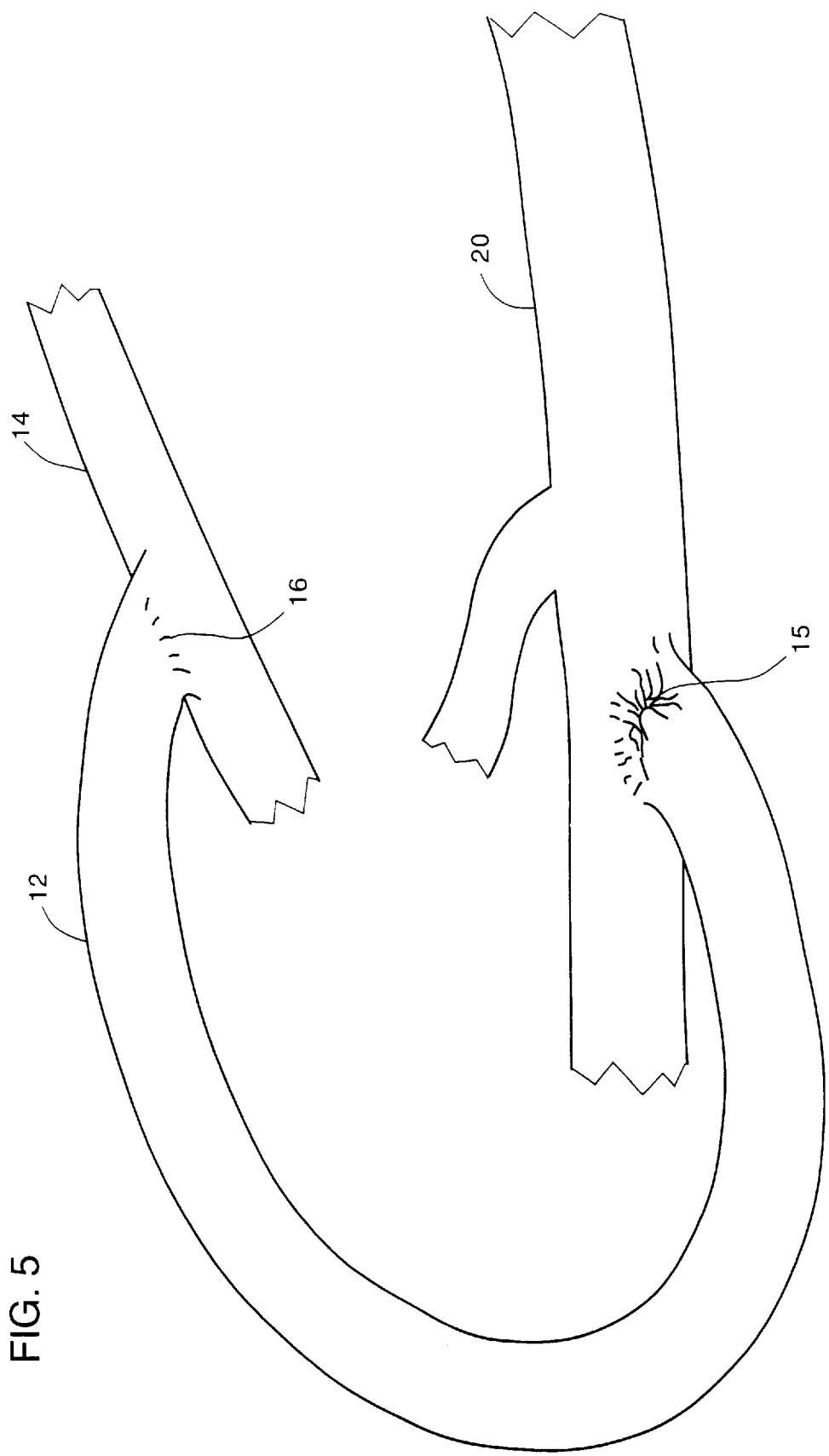
FIG. 5 is a drawing of the artery, vein, and pre-existing graft of FIG. 4 prior to introduction of the catheter according to the invention.
Figure 6:
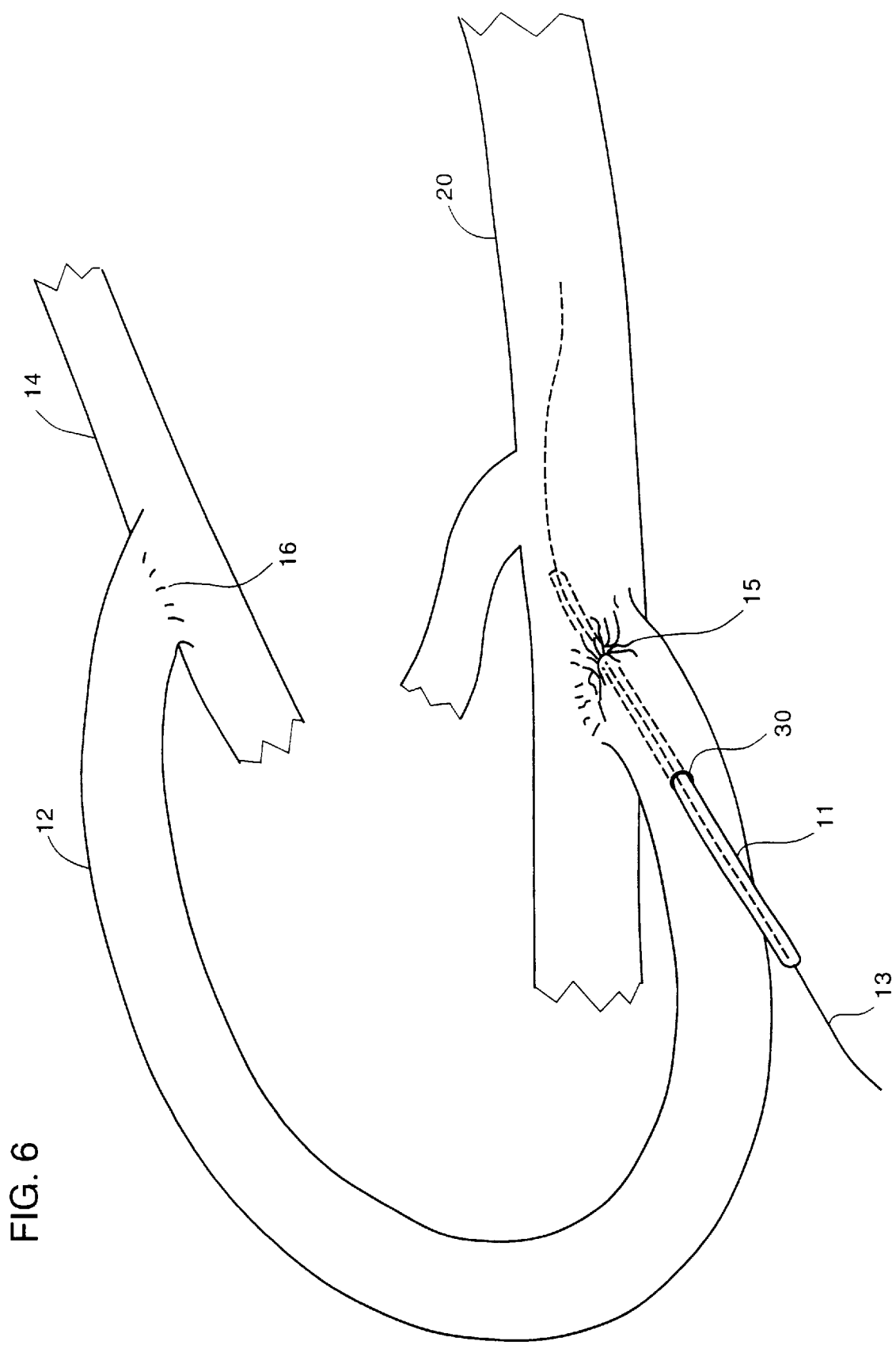
FIG. 6 is a drawing of the artery, vein, and pre-existing graft of FIG. 5 in which a guidewire has been inserted through an incision in the vein in order to permit a catheter according to the invention to be introduced though the wall of the graft.
Figure 7:
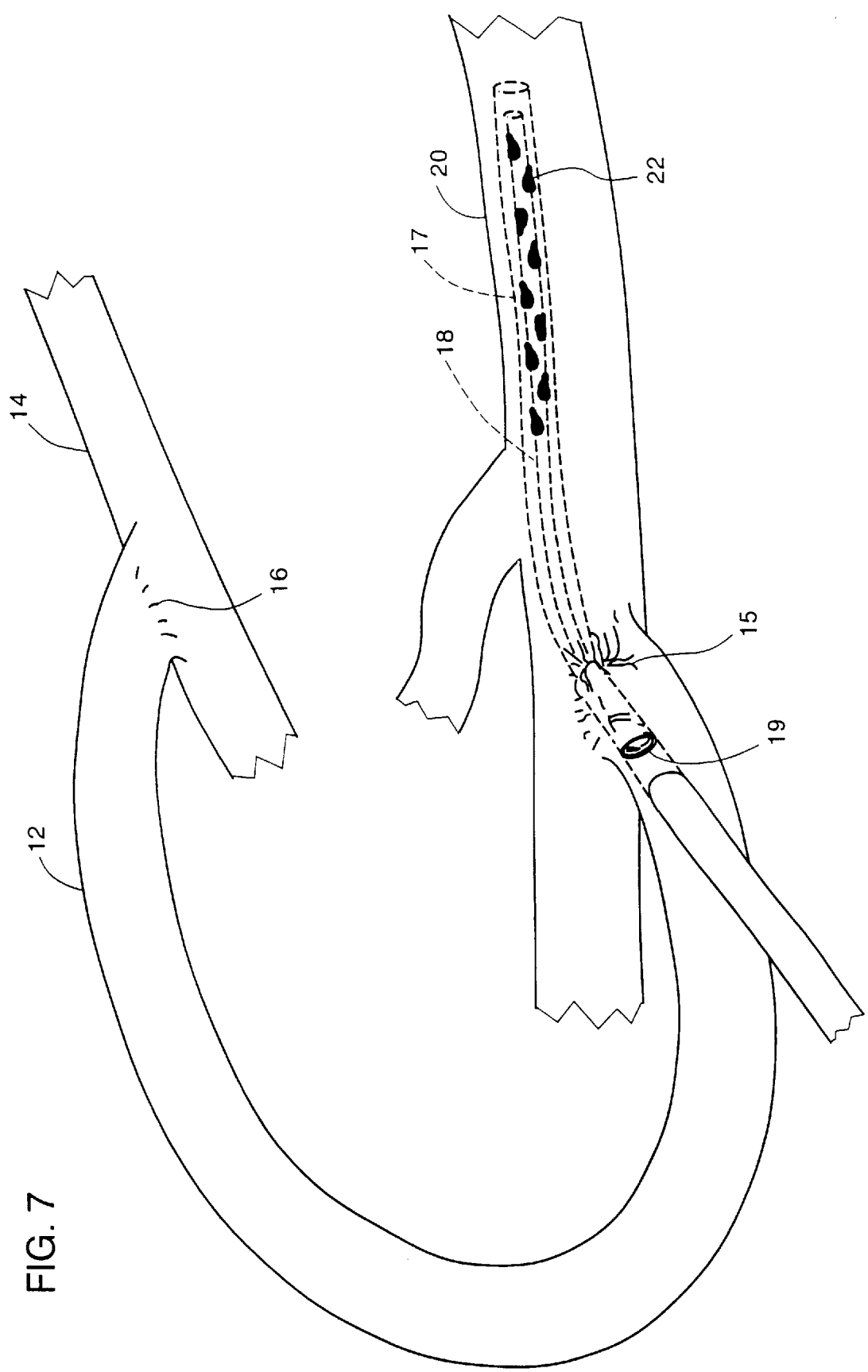
FIG. 7 is a drawing of the artery, vein, and graft of FIG. 5, further showing the catheter according to the invention inserted through the wall of the graft prior to removal of a sheath that encloses the catheter.

As shown in FIG. 4, another procedure according to the invention enables an existing graft 12 to be salvaged by insertion of catheter 18 through the wall of existing graft 12, which is desirable in situations in which clotting associated with a failing graft is not too extensive, as is exemplified by the partially occluded opening 15 into vein 20 shown in FIG. 5. As shown in FIG. 6, according to this procedure, graft 12 is percutaneously cannulated by passage of a needle 11 through an incision 30 into graft 12 and vein 20, and a guidewire 13 is passed through needle 11 into vein 20. Partially occluded vein opening 15 is dilated by angioplasty, and a sheath 17 is inserted percutaneously through graft 12 (FIG. 7) and into vein 20. Catheter 18 within sheath 17 includes a collapsible funnel-shaped portion 19. When sheath 17 is removed from graft 12 and vein 20, funnel-shaped portion 19 opens up within graft 12 as is shown in FIG. 4. Holes 22 of catheter 18 are positioned within vein 20 (FIG. 7). Because catheter 18 has a funnel configuration, the outer wall of funnel-shaped portion 19 of catheter 18 engages the inner wall of graft 12. Funnel-shaped portion 19 of catheter 18 lies within pre-existing graft 12, and the slim end (tail) of catheter 18 lies within the interior of vein 20. Blood bypasses the interconnection of graft 12 and catheter 18 by flowing through catheter 18 and out of holes 22.

There has been described novel and improved apparatus and techniques for interconnecting an artery and vein. It is evident that those skilled in the art may now make numerous uses and modifications of and departures from the specific embodiment described herein without departing from the inventive concept. The invention is to be construed as embracing each and every novel feature and novel combination of features present in or possessed by the apparatus and technique herein disclosed and limited solely by the spirit and scope of the appended claims.

What is claimed is:

1. An apparatus for interconnecting an artery and a vein, comprising:

a graft of biocompatible material;

a catheter of biocompatible material;

the graft having an end configured for attachment to the artery and another end configured for interconnection with the catheter;

the catheter having an end configured for interconnection with the end of the graft that is configured for interconnection with the catheter and having a plurality of holes spaced axially therefrom that are positionable within the interior of the vein, at least some of the holes being located in a side wall of the catheter, while the graft is attached to the artery, such that the plurality of holes are spaced from an opening of the vein through which the catheter passes into the vein, and such that the catheter within the vein has a diameter smaller than an inner diameter of the vein;

the plurality of holes providing an outlet within the interior of the vein for blood from the artery that passes through the graft and the catheter; the plurality of holes being sized and numbered so as to minimize scarring and stenosis by minimizing flow turbulence, due to blood exiting through the holes at locations downstream from a sensitive area at the opening of the vein.

2. The apparatus of claim 1 wherein the graft and the catheter are mechanically interconnectable.

3. The apparatus of claim 1 wherein the graft and catheter are manufactured to be integral with each other.

4. The apparatus of claim 1 wherein the catheter comprises polytetraflouroethylene.

5. The apparatus of claim 1 wherein the graft has an end configured for attachment to the artery by suturing.

6. The apparatus of claim 1 wherein the catheter is configured for attachment by suturing to the opening in the vein through which the catheter passes.

7. The apparatus of claim 1 wherein the catheter is configured to pass through the opening in the vein without suturing.

8. The apparatus of claim 1 wherein the plurality of holes are positionable within the interior of the vein at a location distal of a vein branch located between the opening in the vein through which the catheter passes and the plurality of holes.

9. The apparatus of claim 1 wherein the graft is constructed to receive repeatedly needles that are insertable into the graft.

10. The apparatus of claim 9 wherein the graft is constructed to receive repeatedly needles constructed to convey blood for hemodialysis.

11. The apparatus of claim 1 wherein the graft and the catheter are both constructed to remain subcutaneously within a patient's body.

12. The apparatus of claim 1 wherein at least a portion of the catheter has a funnel configuration and wherein an outer wall of the portion of the catheter having the funnel configuration engages an inner wall of the graft to form the interconnection between the catheter and the graft.

13. The apparatus of claim 1 wherein the end of the graft configured for interconnection with the catheter is configured for direct interconnection with the catheter and the end of the catheter configured for interconnection with the graft is configured for direct interconnection with the graft.

14. The apparatus of claim 13 wherein the catheter is tapered from a larger diameter at the end of the catheter configured for interconnection with the graft to a smaller diameter spaced axially from the end of the catheter configured for interconnection with the graft.

15. A catheter of biocompatible material for salvaging a graft of biocompatible material interconnecting an artery and a vein, comprising;
a portion having a funnel configuration and configured for engaging an inner wall of the graft, outside of the vein, thereby allowing an interconnection between the catheter and the graft that is external to the vein;
a portion configured for insertion into the vein, having at least one hole spaced axially from the portion having the funnel configuration, the at least one hole being positionable within the interior of the vein, while the graft is attached to the artery, such that the hole is spaced from an opening of the vein through which the catheter passes into the vein, the at least one hole providing an outlet within the interior of the vein for blood from the artery that passes through the graft and the catheter.

16. A method of interconnecting an artery and a vein, comprising the steps of:
providing a graft of biocompatible material;
providing a catheter of biocompatible material;
the graft having an end configured for attachment to the artery and another end configured for interconnection with the catheter;
the catheter having an end configured for interconnection with the end of the graft that is configured for interconnection with the catheter;
creating an opening in the vein;
causing the catheter to pass through the opening of the vein so that a plurality of holes in the catheter are positioned within the interior of the vein and spaced from the opening, at least some of the holes being located in a side wall of the catheter, the catheter within the vein having a diameter smaller than an inner diameter of the vein;
creating an opening in the artery;
attaching the artery to the graft;
allowing blood from the artery to pass through the graft and catheter, interconnected with each other, and out of the plurality of holes in the catheter into the interior of the vein; the plurality of holes being sized and numbered so as to minimize scarring and stenosis by minimizing flow turbulence, due to blood exiting through the holes at locations downstream from a sensitive area at the opening of the vein.

17. The method of claim 16 wherein the step of attaching the artery to the graft comprises suturing.

18. The method of claim 16 further comprising the step of attaching the catheter by suturing to the opening in the vein through which the catheter passes.

19. The method of claim 16 wherein the step of allowing blood from the artery to pass through the graft and catheter is performed without suturing between the catheter and the opening in the vein.

20. The method of claim 16 wherein the end of the graft configured for interconnection with the catheter is configured for direct interconnection with the catheter and the end of the catheter configured for interconnection with the graft is configured for direct interconnection with the graft.

21. The method of claim 20 wherein the catheter is tapered from a larger diameter at the end of the catheter configured for interconnection with the graft to a smaller diameter spaced axially from the end of the catheter configured for interconnection with the graft.

22. A method of interconnecting an artery and a vein, comprising the steps of:
providing a graft of biocompatible material;
providing a catheter of biocompatible material;
the graft and the catheter being configured for interconnection with each other;
creating an opening in the vein;
causing the catheter to pass through the opening of the vein so that a plurality of holes in the catheter are positioned within the interior of the vein and spaced from the opening, at a location distal of a vein branch located between the opening in the vein through which the catheter passes and the plurality of holes, at least some of the holes being located in a side wall of the catheter, the catheter within the vein having a diameter smaller than an inner diameter of the vein;
creating an opening in the artery;
attaching the artery to the graft;
allowing blood from the artery to pass through the graft and catheter, interconnected with each other, and out of the plurality of holes in the catheter into the interior of the vein; the plurality of holes being sized and numbered so as to minimize scarring and stenosis by minimizing flow turbulence, due to blood exiting through the holes at locations downstream from a sensitive area at the opening of the vein.

23. A method of interconnecting an artery and a vein, comprising the steps of:

providing a graft of biocompatible material;

providing a catheter of biocompatible material;

the graft having an end configured for attachment to the artery and another end configured for interconnection with the catheter;

the catheter having an end configured for interconnection with the end of the graft that is configured for interconnection with the catheter;

creating an opening in the vein;

causing the catheter to pass through the opening of the vein so that a plurality of holes in the catheter are positioned within the interior of the vein and spaced from the opening;

creating an opening in the artery;

attaching the artery to the graft;

allowing blood from the artery to pass through the graft and catheter, interconnected with each other, and out of the plurality of holes in the catheter into the interior of the vein; the plurality of holes being sized and numbered so as to minimize scarring and stenosis by minimizing flow turbulence; and repeatedly inserting needles into the graft.

24. The method of claim 23 further comprising the step of allowing blood to be conveyed through the needles for hemodialysis.

25. A method of salvaging a graft of biocompatible material interconnecting an artery and a vein, comprising the steps of:

providing a catheter of biocompatible material configured for interconnection with the graft;

causing the catheter to pass through a wall of the graft until at least one hole in the catheter is positioned within the interior of the vein and spaced from a point of interconnection between the graft and the vein;

engaging the catheter with an interior wall of the graft, outside of the vein, thereby interconnecting the catheter with the graft externally of the vein; and allowing blood from the artery to pass through the graft and catheter, interconnected with each other, and out of the at least one hole in the catheter into the interior of the vein.

26. The method of claim 25 further comprising the step of positioning the at least one hole within the interior of the vein at a location distal of vein branch located between the opening in the vein through which the catheter passes and the at least one hole.

27. The method of claim 25 wherein at least a portion of the catheter has a funnel configuration, and wherein an outer wall of the catheter engages an inner wall of the graft to form the interconnection between the catheter and the graft.

28. A method of salvaging a graft of biocompatible material interconnecting an artery and a vein, comprising the steps of:

providing a catheter of biocompatible material configured for interconnection with the graft;

causing the catheter to pass through a wall of the graft until at least one hole in the catheter is positioned within the interior of the vein and spaced from a point of interconnection between the graft and the vein;

engaging the catheter with an interior wall of the graft, thereby interconnecting the catheter with the graft;

allowing blood from the artery to pass through the graft and catheter, interconnected with each other, and out of the at least one hole in the catheter into the interior of the vein; and repeatedly inserting needles into the graft.

29. The method of claim 28 further comprising the step of allowing blood to be conveyed through the needles for hemodialysis.

30. An apparatus for interconnecting an artery and a vein, comprising:

a graft of biocompatible material;

a catheter of biocompatible material;

the graft having an end configured for attachment to the artery and another end configured for direct interconnection with the catheter;

the catheter having an end configured for direct interconnection, outside of the vein, with the end of the graft that is configured for direct interconnection with the catheter, thereby providing an interconnection between the catheter and the graft that is external to the vein, and having at least one hole spaced axially therefrom that is positionable within the interior of the vein, while the graft is attached to the artery, such that the hole is spaced from an opening of the vein through which the catheter passes into the vein;

the at least one hole providing an outlet within the interior of the vein for blood from the artery that passes through the graft and the catheter;

the catheter being tapered from a larger diameter at the end of the catheter configured for direct interconnection with the graft to a smaller diameter spaced axially from the end of the catheter configured for direct interconnection with the graft.

31. The apparatus of claim 30 wherein the catheter comprises a funnel-shaped portion.

32. The apparatus of claim 30 wherein the at least one hole comprises a plurality of holes sized and numbered so as to minimize scarring and stenosis by minimizing flow turbulence.

33. The apparatus of claim 30 wherein the catheter is configured to pass through the opening in the vein without suturing.

34. A method of interconnecting an artery and a vein, comprising the steps of:

providing a graft of biocompatible material;

providing a catheter of biocompatible material;

the graft having an end configured for attachment to the artery and another end configured for direct interconnection with the catheter;

the catheter having an end configured for direct interconnection, outside of the vein, with the end of the graft that is configured for direct interconnection with the catheter, thereby providing an interconnection between the catheter and the graft that is external to the vein;

creating an opening in the vein;

causing the catheter to pass through the opening of the vein so that at least one hole in the catheter is positioned within the interior of the vein and spaced from the opening;

creating an opening in the artery;

attaching the artery to the graft;

allowing blood from the artery to pass through the graft and catheter, interconnected directly with each other, and out of the at least one hole in the catheter into the interior of the vein;

the catheter being tapered from a larger diameter at the end of the catheter configured for direct interconnection with the graft to a smaller diameter spaced axially from the end of the catheter configured for direct interconnection with the graft.

35. The method of claim 34 wherein the catheter comprises a funnel-shaped portion.

36. The method of claim 34 wherein the at least one hole comprises a plurality of holes sized and numbered so as to minimize scarring and stenosis by minimizing flow turbulence.

37. The method of claim 34 wherein the step of allowing blood from the artery to pass through the graft and catheter is performed without suturing between the catheter and the opening in the vein.

* * * * *